United States Patent [19]

Masai et al.

[11] Patent Number: 4,975,535

[45] Date of Patent: Dec. 4, 1990

[54] METHOD FOR PERPARING PARTICULATE SACCHARIDES

[75] Inventors: Teruhisa Masai, Yokohama; Takanobu Shibuta, Machida, both of Japan

[73] Assignee: The Calpis Food Industry Co., Ltd., Tokyo, Japan

[21] Appl. No.: 341,950

[22] Filed: Apr. 24, 1989

[30] Foreign Application Priority Data

Apr. 25, 1988 [JP] Japan ................................ 63-100250

[51] Int. Cl.[5] ........................ C07G 3/00; C07G 17/00; C07H 1/00; A61K 31/00

[52] U.S. Cl. ...................................... 536/124; 536/4.1

[58] Field of Search .................. 536/124, 4.1; 514/25, 514/53, 54

[56] References Cited

U.S. PATENT DOCUMENTS 4,717,765 1/1988 Hirao et al. ........................ 536/124

4,816,445 3/1989 Mitsuhashi et al. ................ 536/102

*Primary Examiner*—Ronald W. Griffin

*Assistant Examiner*—Everett White

*Attorney, Agent, or Firm*—Keil & Weinkauf

[57] ABSTRACT

A method for preparing particulate saccharides comprises drying a solution containing at least two kinds of saccharides followed by melting the at least two kinds of saccharides, and cooling and pulverizing the saccharides to obtain the particulate saccharides.

16 Claims, No Drawings

METHOD FOR PERPARING PARTICULATE SACCHARIDES

BACKGROUND OF THE INVENTION

This invention relates to a method for preparing particulate saccharides and, more particularly, to a method for preparing particulate saccharides containing two or more saccharides that can be crystallized only with difficulty.

A method of preparing particulate saccharides is known in which a solution containing saccharides is concentrated and cooled, whereupon the formed saccharide crystals are separated and dried. The process, however, is limited to saccharides that can be crystallized easily, such as glucose or sucrose.

On the other hand, those saccharides that are difficult to crystallize industrially are handled in the form of a highly concentrated solution. However, it is costly to transport saccharides in the form of solutions. Further, saccharides in the form of solutions cannot be used for powdered foods, thus restricting the use of such materials.

It is known to dry two or more saccharides which are difficult to crystallize, such as saccharides containing oligosaccharides or honey, by spray drying, vacuum freeze drying and vacuum drying methods.

When spray drying a solution of saccharides of high concentration and high viscosity that can be crystallized difficultly, it is necessary to lower the concentration of the solution of the saccharides to be sprayed by, for example, adding water to the solution. It is also necessary to add excipiens, such as dextrin, to the solution, so that much heat is needed in drying. The produced powdered saccharides are also not satisfactory in that they are low in purity while being low in sweetness and poor in flavor.

In vacuum freeze drying a solution of saccharides of high concentration and high viscosity that can be crystallized difficultly, it also is necessary to lower the concentration of the solution of saccharides, in a manner similar to the above described spray drying. This fact plus the required freezing and warming, creates economic disadvantages.

On the other hand, the vacuum drying method has a drawback that, although it is possible to use a solution containing the saccharides as a starting material in high concentration and in high density, the produced saccharides are low in bulk density. To overcome this drawback, a method of granulating the particulate saccharides by dry agglomeration has been proposed. However, in this dry agglomeration, problems are presented in that the solubility of the produced saccharides is lowered.

SUMMARY OF THE INVENTION

It is a principal object of the present invention to provide a method for preparing particulate saccharides having a high bulk density, excellent solubility and good flavor.

It is another object of the present invention to provide an economically effective method for preparing particulate saccharides.

It is yet another object of the present invention to provide a method for preparing particulate saccharides for affording certain physiological effects such as regulating the intestines and for augmenting the sweetness.

The above and other objects of the invention will become apparent from the following description.

According to the present invention, a method is provided for preparing particulate saccharides comprising drying a solution containing at least two kinds of saccharides followed by melting the at least two kinds of saccharides, and cooling and pulverizing the saccharides to obtain the particulate saccharides.

PREFERRED EMBODIMENTS OF THE INVENTION

The present invention is directed to an efficient and economically advantageous method for preparing particulate saccharides having high bulk density, solubility and flavor from a solution containing two or more kinds of saccharides, above all, a starting solution containing saccharides that can be crystallized difficultly.

According to the present invention, the saccharides employed as the starting material are two or more different kinds of saccharides. Above all, two or more different kinds of saccharides of the same or different species selected from the group of monosaccharides, disaccharides and oligosaccharides, namely trisaccharides, tetrasaccharides, pentasaccharides and hexasaccharides, are most preferred.

The monosaccharides include glucose, fructose, galactose, pinitol and xylose.

The disaccharides include sucrose, maltose, galactopinital and lactose.

The oligosaccharides such as trisaccharides to hexasaccharides include for example stachyose, raffinose, maltotriose, maltotetraose, panose, nystose, 1-kestose, and galactosyl-lactose.

The two or more different kinds of saccharides employed in accordance with the present invention may be a combination of the same or different species of the above saccharides and thus may consist of the combination of the same species, such as, for example, the combination of monosaccharides-monosaccharides or oligosaccharides-oligosaccharides, or of the combination of the different species, such as, for example, the combination of two or more species selected from the group of mono-, di- and oligosaccharides. In the case of the latter combination consisting of different species of saccharides, two or more saccharides may be selected from the same species of saccharides in combination with at least one selected from the other species.

The commercially available mixtures of the above sugar, isomerized saccharides and natural products, such as honey, may be used directly or as a mixture with mono-, di- or oligosaccharides.

The relative contents of the saccharides may be optionally selected according to usages and applications. It is, however, preferred that the minimum and maximum contents in the solution containing the two or more saccharides of each of the two or more saccharides calculated as solids be not less than 4 wt. % and not more than 96 wt. %, respectively.

The concentration of the aqueous solution of the above two or more saccharides need only be within the range suited for the subsequent drying process and usually may be within the range preferably from 40 to 85 wt. % and more preferably from 60 to 80 wt. % as total solids.

The above solution is then dried or dehydrated and compacted or solidified to produce a solid product. Drying is performed under an atmospheric pressure or in vacuum. The vacuum heating and drying method is preferred. This vacuum heating and drying method may be performed by the usual vacuum drying method, the preferred drying conditions being at vacuum of 1 to 70 Torr and a temperature of 30° to 160° C.

The solid product thus produced is then melted by heating it. Since the two or more saccharides are contained in the solid product, melting point depression takes place, i.e. the melting point of the product as a whole is lowered. By the melting point depression, the solid product is melted at a temperature lower than the melting point of each of the saccharides contained in the product. In this manner, it is possible to prevent the deterioration of the produced particulate saccharides due to heating, while an economic advantage is derived in that the heat necessary for melting is reduced as compared with the case of melting each component saccharide. Although there is no limitation to the melting temperature, the temperature of 40° to 170° C. is preferred. When the saccharides such as honey or isomerized sugar are used as the starting material, the aforementioned drying and melting may be performed continuously. The drying and melting may be performed preferably under the vacuum of 3 to 20 Torr and at the temperature of 70° to 130° C.

The melted saccharide product obtained by the above process may be solidified by cooling preferably below the melting point of the product. The produced solid product is then crushed by a crusher such as a flash mill and passed through a shifter, etc. to produce the particulate saccharides having the desired particle size.

There is no limitation to the particle size of the particulate saccharides which may be optionally adjusted in accordance with the intended usages and application. When easy handling and high solubility are desired, the lesser particle size may be employed. Usually, the particle size of 0.1 to 4.7 mm and preferably not more than 1.7 mm is preferred.

The thus produced particulate saccharide product may be handled easily since it has a bulk density as large as, for example, 1.2 to 3 times those of the known saccharide products, high solubility and the water contents of not more than 1 wt. %.

According to the present invention, particulate saccharides having high bulk density, solubility and flavor may be produced by drying and solidifying a solution containing two or more saccharides to produce a solid product and further heating and melting the solid product followed by cooling and crushing of the resulting product.

The particulate saccharides produced by the method of the present invention may be advantageously employed for affording certain physiological effects such as intestine regulation and augmenting the sweetness.

In addition, according to the method of the present invention, melting may be performed at a temperature lower than the melting point of each saccharide contained in the starting solution, so that the melted product may be exempt from thermal deterioration caused by heating and hence particulate saccharides of excellent quality may be produced.

EXAMPLES OF THE INVENTION

The present invention will be explained in more detail with reference to Examples and Comparative Examples. It is, however, noted that these Examples are given only for illustration and are not intended for limiting the scope of the invention.

EXAMPLE 1

200 g of a solution of soya bean oligosaccharides having a concentration of 76 wt. % and containing solid contents in accordance with the following composition:

| | |
|---|---|
| stachyose | 24 wt. % |
| raffinose | 7 wt. % |
| sucrose | 45 wt. % |
| other saccharides* | 24 wt. % |
| | 100 wt. % (solid contents) |

*monosaccharides derived from soya bean (glucose, fructose and pinitol) and disaccharides (galactopinitol)

The above solution was dried by a vacuum belt drier manufactured by HISAKA WORKS LTD. under the trade name of SWEL-VAQ type at 90° C. for 60 minutes under a vacuum of 3 to 5 Torr to produce puff-like dry powders. The produced dry powders were heated further at 116° C., melted, cooled at room temperature, crushed and adjusted to a particle size of 12 to 42 mesh (1.40 to 0.35 mm) to produce 122 g of particulate saccharides having water contents of 0.4 wt. %.

COMPARATIVE EXAMPLE 1

200 g of the soya bean oligosaccharide solution having the same composition as that in Example 1 was dried in the same way as in Example 1 to produce puff-like dry powders. These dry powders were crushed and adjusted to the particle size of 12 to 42 mesh to produce 130 g of puff-type particulate saccharides.

COMPARATIVE EXAMPLE 2

200 g of the soya bean oligosaccharide solution having the composition same as that in Example 1 was dried in the same way as in Example 1 to produce puff-like dry powders. After applying the pressure of 70 $kg/cm^2$ to the produced dry powders, the powders were crushed and adjusted to the particle size of 12 to 42 mesh to produce 93 g of dry agglomerated type granular saccharides.

The bulk density and the speed of dissolution of the saccharides produced in Example 1 and Comparative Examples 1 and 2 were measured by the methods described below. The results are shown in Tables 1 and 2.

MEASUREMENT OF BULK DENSITY 100 ml of the saccharides obtained in Example 1 and Comparative Examples 1 and 2 were charged into a beaker. These saccharides were introduced into a 30 ml cylinder via a funnel of a unit for measuring the bulk density (JIS K5101; manufactured by KURAMOCHI KAGAKUKIKAI LTD.). The saccharides other than those introduced into the cylinder were discarded and the weight was then measured to find the bulk density. The measurement operations were repeated five times to find the mean value.

TABLE 1

| | Comp. Ex. 1 | Comp. Ex. 2 | Ex. 1 | Ref. Ex. |
|---|---|---|---|---|
| No. 1 | 6.5 g | 19.3 g | 22.2 g | 22.6 g |
| No. 2 | 6.0 | 19.3 | 22.0 | 22.6 |
| No. 3 | 6.2 | 19.2 | 22.1 | 22.4 |
| No. 4 | 6.2 | 19.2 | 21.8 | 22.6 |
| No. 5 | 6.2 | 19.3 | 22.1 | 22.4 |
| Mean Value | 6.22 g | 19.26 g | 22.04 g | 22.52 g |

TABLE 1-continued

| | Comp. Ex. 1 | Comp. Ex. 2 | Ex. 1 | Ref. Ex. |
|---|---|---|---|---|
| Bulk Density | 0.207 | 0.624 | 0.735 | 0.751 |

(note: In the Reference Example, fine granulated sugar adjusted to the particle size of 12 to 42 mesh was employed)

The product of Comparative Example 1 was puff-like and had a bulk density lower than that of the other Examples. The product of Example 1 had a bulk density higher than that of the Comparative Example 2 and equivalent to that of the fine granulated sugar.

MEASURE OF THE DISSOLUTION SPEED 100 ml of water at 50° C. was taken into a beaker fitted with a stirrer bar which was driven into rotation by a magnetic stirrer at about 150 rpm. 6 g each of the produced saccharides was introduced into the beaker and the time measurement operation was started simultaneously. The time elapsed until the sample was dissolved completely was measured. The measurement operation was repeated three times to find the mean value.

TABLE 2

| | Comp. Ex. 2 | Ex. 1 | Ref. Ex. |
|---|---|---|---|
| No. 1 | 1 min. 18 sec. 1 | 43 sec. 5 | 47 sec. 9 |
| No. 2 | 1 min. 10 sec. 2 | 48 sec. 6 | 52 sec. 3 |
| No. 3 | 1 min. 8 sec. 3 | 49 sec. 8 | 55 sec. 7 |
| Mean Value | 1 min. 12 sec. 2 | 47 sec. 3 | 52 sec. 0 |

EXAMPLE 2

200 g of a 75 wt. % solution containing a mixture of fructoligosaccharides in accordance with the following composition:

| | |
|---|---|
| fructoligosaccharides | 57 wt. % |
| sucrose | 12 wt. % |
| glucose | 31 wt. % |
| | 100 wt. % (solid contents) |

(note: The fructoligosaccharides described in "THE STANDARDS OF HEALTH FOODS" page 49, issued by Japan Health Foods Association on September 1, 1987 were employed.)

The above solution was dried using the same method and the same vacuum belt drier as in Example 1 to produce puff-like dry powders. These powders were further heated and melted at 95.4° C., cooled at room temperature, crushed and adjusted to the particle size of 12 to 42 meshes to produce 114 g of particulate saccharides having water contents of 0.9 wt. %.

COMPARATIVE EXAMPLE 3

200 g of the fructoligosaccharide solution having the same composition as that in Example 2 was dried in the same way as in Example 2 to produce puff-like dry powders. After applying the pressure of 70 kg/cm$^2$ to the produced dry powders, the powders were crushed and adjusted to the particle size of 12 to 42 mesh to produce 90 g of dry agglomerated type granular saccharides.

The dissolution speeds of the saccharides produced in Example 2 and Comparative Example 3 were measured in the same way as in Example 1. The results are shown in the following Table 3. It is noted that the bulk density of the particulate saccharides of Example 2 was measured and found to be about equal to that of Example 1.

TABLE 3

| | Comp. Ex. 3 | Ex. 2 |
|---|---|---|
| No. 1 | 7 min. 8 sec. | 52 sec. 7 |
| No. 2 | 8 min. 11 sec. | 51 sec. 7 |
| No. 3 | 7 min. 46 sec. | 52 sec. 5 |
| Mean Value | 7 min. 42 sec. | 52 sec. 3 |

EXAMPLE 3

200 g of a 75 wt. % solution was prepared containing a mixture of isomaltoligosaccharides having the following composition:

| | |
|---|---|
| isomaltoligosaccharides | 52 wt. % |
| maltose | 6.5 wt. % |
| maltotriose | 0.5 wt. % |
| fructose | 1.0 wt. % |
| glucose | 40 wt. % |
| | 100 wt. % (solid contents) |

(note: The isomaltoligosaccharides described in "THE STANDARDS OF HEALTH FOODS" page 53, issued by Japan Health Foods Association on September 1, 1987 were employed)

The above solution was dried using the same method and the same vacuum belt drier as in Example 1 to produce puff-like dry powders. These powders were further heated and melted at 100° C., cooled at room temperature, crushed and adjusted to the particle size of 12 to 42 mesh to produce 117 g of particulate saccharides having water contents of 0.8 wt. %.

COMPARATIVE EXAMPLE 4

200 g of the isomaltoligosaccharide solution having the same composition as that in Example 3 was dried in the same way as in Example 3 to produce puff-like dry powders. After applying the pressure of 70 kg/cm$^2$ to the produced dry powders, the powders were crushed and adjusted to the particle size of 12 to 42 mesh to produce 92 g of dry agglomerated type granular saccharides.

The dissolution speeds of the saccharides produced in Example 3 and Comparative Example 4 were measured in the same way as in Example 1. The results are shown in the following Table 4. It is noted that the bulk density of the particulate saccharides of Example 3 was measured and found to be about equal to that of Example 1.

TABLE 4

| | Comp. Ex. 4 | Ex. 3 |
|---|---|---|
| No. 1 | 1 min. 34 sec. | 55 sec. 8 |
| No. 2 | 1 min. 21 sec. | 51 sec. 9 |
| No. 3 | 1 min. 41 sec. | 55 sec. 6 |
| Mean Value | 1 min. 32 sec. | 52 sec. 4 |

EXAMPLE 4

200 g of a commercially available honey with the solid contents of 78 wt. % were dried and melted by heating at 120° C. for 20 minutes under the vacuum of 3 to 5 Torr, using the vacuum belt drier similar to that in Example 1. The melted product was cooled at room temperature, crushed and adjusted to the particle size of 12 to 42 mesh (1.40 to 0.35 mm) to produce 125 g of the particulate honey having water contents of 0.5 wt. %.

As compared with the commercially available particulate honey, the produced particulate honey had high flavor because of its high purity.

EXAMPLE 5

200 g of commercially available high fructose corn syrup having a solid contents of 75 wt. % were dried and melted by heating in the same way as in Example 4. The melted product was cooled at room temperature, crushed and adjusted to the particle size of 12 to 42 mesh to produce 119 g of the particulate saccharides.

While high fructose corn syrups on the market are in the form of solution, the method of the present invention makes it possible to produce the high fructose corn syrup in the form of particles or powders and to provide a product of high purity and flavor.

Although the present invention has been described with reference to the specific examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A method for preparing particulate saccharides comprising drying a solution containing at least two kinds of saccharides followed by melting said at least two kinds of saccharides, and cooling and pulverizing the saccharides to obtain said particulate saccharides, said at least two kinds of saccharides being selected from the group consisting of monosaccharides, disaccharides, oligosaccharides from trisaccharides to hexasaccharides, natural saccharides, isomerized sugar and mixtures thereof.

2. The method according to claim 1 wherein said monosaccharides are selected from the group consisting of glucose, fructose, galactose, pinitol, xylose and mixtures thereof.

3. The method according to claim 1 wherein said disaccharides are selected from the group consisting of sucrose, maltose, isomaltose, lactose, galactopinitol and mixtures thereof.

4. The method according to claim 1 wherein said oligosaccharides from trisaccharides to hexasaccharides are selected from the group consisting of stachyose, raffinose, maltotriose, maltotetraose, panose, nystose, 1-kestose, galactosyl-lactose and mixtures thereof.

5. The method according to claim 1 wherein said natural saccharides are honey.

6. The method according to claim 1 wherein minimum and maximum contents calculated as solid contents of each of said at least two kinds of saccharides in the solution containing said at least two kinds of saccharides are not less than 4 wt. % and not more than 96 wt. %, respectively.

7. The method according to claim 1 wherein concentration of total solids in the solution containing said at least two kinds of saccharides to 40 to 85 wt. %.

8. The method according to claim 1 wherein the drying is performed by a vacuum heating and drying method.

9. The method according to claim 8 wherein said vacuum heating and drying method is performed at a vacuum of 1 to 70 Torr and at a temperature of 30° to 160° C.

10. The method according to claim 1 wherein said melting is performed at a temperature lower than the melting point of each of the saccharides contained in the solution of said saccharides.

11. The method according to claim 10 wherein said melting is performed at a temperature of 40° to 170° C.

12. The method according to claim 1 wherein said drying and said melting are performed continuously.

13. The method according to claim 12 wherein said drying and said melting are performed at a vacuum of 3 to 20 Torr and at a temperature of 70° to 130° C.

14. The method according to claim 1 wherein said cooling is performed below a melting point of the saccharides.

15. The method according to claim 1 wherein a particle size of said particulate saccharides is in the range from 0.1 to 4.7 mm.

16. The method according to claim 1 wherein water contents of the particulate saccharides are not more than 1 wt. %.

* * * * *

UNITED STATES PATENT AND TRADEMARK OFFICE
CERTIFICATE OF CORRECTION

PATENT NO. : 4,975,535

DATED : December 4, 1990

INVENTOR(S) : Teruhisa MASAI et al.

It is certified that error appears in the above-identified patent and that said Letters Patent is hereby corrected as shown below:

On the title page, Item [54] and column 1, lines 1-2, should read

--METHOD FOR PREPARING PARTICULATE SACCHARIDES--

Signed and Sealed this

First Day of June, 1993

Attest:

Michael K. Kirk

MICHAEL K. KIRK

*Attesting Officer*

*Acting Commissioner of Patents and Trademarks*